United States Patent
Romem

(10) Patent No.: US 9,895,105 B2
(45) Date of Patent: Feb. 20, 2018

(54) INDEPENDENT NON-INTERFERING WEARABLE HEALTH MONITORING AND ALERT SYSTEM

(75) Inventor: Yoram Romem, Herzeliya (IL)

(73) Assignee: HEALTHWATCH LTD. (IL)

( * ) Notice: Subject to any disclaimer, the term of this patent is extended or adjusted under 35 U.S.C. 154(b) by 1089 days.

(21) Appl. No.: 14/128,574

(22) PCT Filed: Jun. 19, 2012

(86) PCT No.: PCT/IL2012/000248
§ 371 (c)(1),
(2), (4) Date: Mar. 24, 2014

(87) PCT Pub. No.: WO2012/176193
PCT Pub. Date: Dec. 27, 2012

(65) Prior Publication Data
US 2014/0206948 A1    Jul. 24, 2014

Related U.S. Application Data

(60) Provisional application No. 61/498,736, filed on Jun. 20, 2011, provisional application No. 61/584,823, filed on Jan. 10, 2012.

(51) Int. Cl.
*A61B 5/00* (2006.01)
*A61B 5/0205* (2006.01)
(Continued)

(52) U.S. Cl.
CPC .......... *A61B 5/6804* (2013.01); *A61B 5/0022* (2013.01); *A61B 5/04085* (2013.01);
(Continued)

(58) Field of Classification Search
None
See application file for complete search history.

(56) References Cited

U.S. PATENT DOCUMENTS

| 6,047,203 A * | 4/2000 | Sackner | A41D 13/1281 |
| | | | 600/301 |
| 6,687,523 B1 * | 2/2004 | Jayaramen | A41D 13/1281 |
| | | | 600/388 |

(Continued)

FOREIGN PATENT DOCUMENTS

WO    2006009830 A2    1/2006
WO    2012176193 A1    12/2012

OTHER PUBLICATIONS

International Search Report for International Application No. PCT/IL2012/000248 dated Sep. 13, 2012.

*Primary Examiner* — Brian T Gedeon
(74) *Attorney, Agent, or Firm* — Polsinelli PC

(57) ABSTRACT

A seamless, substantially continuous, independent and wearable health monitoring and self-alert system, configured for use by a living being on a daily basis, including by a healthy living being. The wearable health monitoring and self-alert system includes a garment worn by the living being adjacently to preconfigured portions of the body of the living being. The system further includes a garment-control device that includes a garment-processor and a battery. The system further includes a multi-lead ECG measuring device including multiple electrodes or probe-devices embedded into the garment, and an alerting unit. Preferably, the system further includes multiple sensing devices selected from the group consisting of sensors and electrodes. At least one of the sensing devices is embedded into the garment, wherein each of the sensing devices is configured to detect a predetermined physiological or chemical parameter of the living being.

6 Claims, 10 Drawing Sheets

(51) Int. Cl.
*A61B 5/0408* (2006.01)
*A61B 5/021* (2006.01)

(52) U.S. Cl.
CPC ............ *A61B 5/6805* (2013.01); *A61B 5/021* (2013.01); *A61B 5/0205* (2013.01); *A61B 5/02055* (2013.01); *A61B 2560/0468* (2013.01)

(56) References Cited

U.S. PATENT DOCUMENTS

| | | | | |
|---|---|---|---|---|
| 7,762,953 | B2* | 7/2010 | Derchak | A61B 5/0205 |
| | | | | 600/300 |
| 8,639,348 | B2* | 1/2014 | Geheb | A61N 1/3987 |
| | | | | 128/903 |
| 8,925,392 | B2* | 1/2015 | Esposito | A61B 5/1036 |
| | | | | 73/862.01 |
| 9,381,373 | B2* | 7/2016 | Geheb | A61N 1/3987 |
| 9,566,033 | B2* | 2/2017 | Bogdanovich | A61B 5/6804 |
| 2008/0116189 | A1 | 5/2008 | Fernandez et al. | |
| 2008/0183082 | A1 | 7/2008 | Farringdon et al. | |
| 2010/0185062 | A1 | 7/2010 | Salazar et al. | |
| 2013/0281795 | A1* | 10/2013 | Varadan | A61B 5/02055 |
| | | | | 600/301 |
| 2013/0338472 | A1* | 12/2013 | Macia Barber | A61B 5/04085 |
| | | | | 600/388 |
| 2014/0142459 | A1* | 5/2014 | Jayalth | A61B 5/0022 |
| | | | | 600/547 |
| 2015/0202429 | A1* | 7/2015 | Fritzsche | A61N 1/0484 |
| | | | | 607/48 |
| 2015/0370320 | A1* | 12/2015 | Connor | A61B 5/6831 |
| | | | | 345/173 |

* cited by examiner

INDEPENDENT NON-INTERFERING WEARABLE HEALTH MONITORING AND ALERT SYSTEM

CROSS-REFERENCE TO RELATED APPLICATIONS

This application is a national stage entry PCT/IL2012/000248, which was filed on Jun. 19, 2012, which claims priority to and benefit of U.S. Provisional Application No. 61/584,823, which was filed on Jan. 10, 2012, and U.S. Provisional Application No. 61/498,736, which was filed on Jun. 20, 2011, each of said applications is expressly incorporated herein in its entirety.

This application relates to the PCT/IL2010/000774 ('774), the disclosure of which is included herein by reference in its entirety.

FIELD OF THE INVENTION

The present invention relates to real-time health monitoring systems and more particularly, the present invention relates to an independent wearable, real-time, substantially continuous health monitoring system, carried by a monitored person (or another living being) by wearing special garments, such that the system does not interfere with the everyday life of the monitored living being.

Furthermore, the system of the present invention issues a personal-alert to the monitored person, and possibly to external parties, upon detecting a potentially health hazardous situation. The monitored person does not need to do anything in order to get a personal-alert, but just to wear the special garments (including an undershirt or a bra) that are part of the system and to have the smart-phone at hand. A variety of sensors are embedded and/or integrated into the special garment, thus facilitating the detection of a variety of health related abnormalities, including the main aspects of cardiac hazards such as Arrhythmia, Ischemia, heart failure and more. The sensors are embedded and/or integrated into the special garment and include electrodes for measuring clinical level ECG, preferably, having at least a 12-leads ECG.

An innovative probe device is preferably used to detect a predetermined physiological or chemical parameter of a particular living being, facilitated to compensate for slight displacements of the electrodes on the body (especially when the person is in motion). The probe device includes a multiplicity of electrodes, each providing a sensed-signal, and a probe processor for selecting the best sensed-signal as the output of the probe device.

BACKGROUND OF THE INVENTION AND PRIOR ART

PCT application '774 explains the need for "a health monitoring system, implantable into and/or wearable by a living being to be monitored, wherein the system does not interfere with the everyday life of the monitored living being and issues an alert upon detecting a potentially health hazardous situation or a tendency to develop such situation." Such an "early warning" system, is the subject of the current invention.

As described in '774, there is a need for a health monitoring system that continuously checks the well being of a person (or any other living being) that, typically, is considered healthy (or with a known set of diseases), covering a significant range of health hazards that may cause a significant life style change/limitation, and provides an alert as early as possible—all this, with no significant limitation to the normal life style of the person bearing the system.

Preferably, with no limitation, no special or routine actions are required of the monitored living being in order to be alerted, no special surgery should be required for the system to operate nor should limiting wearable devices be needed, as one of the system's major goals is to facilitate the user of the system to assume his/her normal life until a potentially dangerous health situation occurs or evolves. Naturally, such a system may also be used by a sick person, detecting potential exacerbations or new problems.

Attempts have been made to tailor sensors into a garment, in order to monitor health related parameters of living beings. However such systems either record the signals for future, off-line analysis, or attempt to provide a health diagnosis. The off-line analysis may often prove to be too-late, and the health diagnosis is usually not accurate enough to trigger a definite intervention or instruction to the user.

Furthermore, attempts have been made to tailor sensors into a garment, in order to provide measurements of heart status in real-time. However, those measurements are limited to facilitate detection of various types of arrhythmia cases, but fall short of reliable ischemia detection. Yet furthermore, attempts have been made to send the measured data to a remote monitoring center for analysis and decision about clinical aspects. However, those solutions create a strong dependency on communication, availability of professionals and their attention, sometimes losing critical "time-to-hospitalization" in acute events.

There is therefore a need and it would be advantageous to have an independent system that facilitates measuring health related bodily parameters, preferably including measuring clinical level electrocardiogram (ECG), analyze the data in real-time, while the user is at rest or in motion, and upon detecting abnormal measured parameters, including ischemia hazards, alarms the system carrier to seek medical help. Analogously, it would be advantageous to have a system that serves as a family doctor (or another professional physician) of limited scope, who would have, seeing the abnormal measured parameters, sent the person to the emergency room. Hence, analogously, the innovative system would serve as a 24/7 alerting family doctor for definite "go to hospital" cases.

The term "continuous monitoring", as used herein with conjunction with a health monitoring system, refers to a health monitoring system, facilitated to monitor a living being substantially continuous, day and night, when the monitored living being is awake or asleep, and active in substantially all common activities of such living being.

The term "seamless", as used herein with conjunction with a wearable device, refers to a device that when worn by an average person, wherein the device puts no significant limitation to the normal life style of that person and preferably not seen by anybody when used and not disturbingly felt by the user while wearing it. Furthermore, no activity is required from the monitored person in order for the system to provide a personal-alert when needed. It should be noted that people that pursue non-common life style, such as soldiers in combat zone or in combat training zone, or firefighters in training and action, or athletes in training or competition may utilize non-seamless devices. As the "seamless" characteristics refers also to the user's behavior, the wearable component is preferably an item that is normally worn (e.g., underwear) and not some additional item to be worn just for getting the alert.

The terms "underwear" or "garment", as used herein with conjunction with wearable clothing items, refers to seamless wearable clothing items that preferably, can be tightly worn adjacently to the body of a monitored living being, typically adjacently to the skin, including undershirts, brassiere, underpants, socks and the like. Typically, the terms "underwear" or "garment" refer to a clothing item that is worn adjacently to the external surface of the user's body, under external clothing or as the only clothing, in such way that the fact that there are sensors embedded therein and/or integrated therein, is not seen by any other person in regular daily behavior. An underwear item may also include a clothing item that is not underwear per se, but still is in direct and preferably tight contact with the skin, such as a T-shirt, sleeveless or sleeved shirts, sport-bra, tights, dancing-wear, and pants. The sensors, in such a case, can be embedded in such a way that are still unseen by external people to comply with the "seamless" requirement.

The term "tightly" means that specific portions of the garment where there are electrodes or other sensors that require certain pressure on the body to obtain a satisfactory signal, are designed to be as tight as needed. However, all the other parts of the garment may be not as tight. Optionally, there is a provision to facilitate tightening or releasing certain portions of the garment, by built-in straps or other tightening means, so that the need for more or less tightness does not require the replacement of the whole garment.

The term "independent" as used herein with conjunction with a garment, having a wearable device or a health monitoring system, refers to an item that does not depend on any external entity, such as remote monitoring center, but may operationally depend on another regular common personal item of the same user, such as a personal mobile device having a garment-control application, being part of the health monitoring system. It should be noted that if the monitored living being is not a human being, the personal mobile device is carried by the care-taker of the monitored living being. It should be noted that in the case of an animal, the seamless feature is of lesser importance.

The term "abnormal", as used herein with conjunction with health related parameters, refers to a parameter value or one or more ranges of values which are defined as health hazardous or as potential health hazardous, when a trend is identified, and requires attention. For example, the normal blood pressure of an adult person is in the range 120/80 mm Hg. Typically, a systolic blood pressure of 130 mm Hg would not be considered hazardous. However, if a person has a stable mean blood pressure of around $85\pm10$ mm Hg, and suddenly it increases to $125\pm10$ mm Hg, this may be considered as an abnormal situation. Likewise, if the mean blood pressure changes gradually and consistently from 85 mm Hg to 120 mm Hg, in a clear trend, a personal-alert should be issued. The threshold value from which the high blood pressure parameter is considered as health hazardous may vary and can be set personally and optionally, dynamically updated, either manually or automatically, by an adaptation algorithm. Once the high blood pressure parameter, in the above example, is set, any value out of the set threshold value will then be considered as abnormal for that person.

The phrase "clinical level ECG", as used herein with conjunction with ECG measurements, refers to the professionally acceptable number of leads, sensitivity and specificity needed for a definite conclusion by most cardiology physicians to suspect a risky cardiac problem (for example, arrhythmia, myocardial ischemia, heart failure) that require immediate further investigation or intervention. Currently, it is at least a 12-leads ECG and preferably 15-lead ECG, coupled with a motion/posture compensation element, and a real-time processor with adequate algorithms.

The term "personal-alert", as used herein, is a notification issued to the specific user after detecting a health risk hazard by a system according to the present invention. The personal-alert issued by the system is substantially similar to a decision of a family doctor or another professional physician who would have taken, seeing the abnormal measured parameters, in order to instruct further investigation or intervention. The term "specific user" as used herein, means that the personal-alert decision is preferably made while taking into consideration the history of indications, treatments and personal situation of the user, including personal preferences and other personally adapted considerations.

A number of systems that analyze a cardiac patient's condition are commonly used. Such systems include some form of ECG electrodes ("probes") that are removably attached adjacent to the patient's body and are connected to the system. Typically, the electrodes are securely attached to the patient's body at a selected location by suction cups, pads having two-sided glue and other attaching means that can be securely attached to the patient's body and forcedly removed when the measurements are concluded. Thereby, the electrode remains attached to the patient's body at a specific location during the time of measurement, which time is very limited and typically lasts a few minutes up to a few hours.

Also, typically, either a physician or a nurse is responsible for the actual placement of the electrodes at the specific points known to be adequate for accurate ECG measurements.

However, when using a wearable, continuous real-time health monitoring system, worn by a monitored person thereby placing the probes just by wearing, a sensor that is built into garment remains in the vicinity of a specific target bodily location of the monitored person. However, still, there are some changes in the relative position of the sensor with respect to a specific bodily target location of the monitored patient, due to relative movements of the garment, carrying the sensor, with respect to the body of the monitored patient, or due to the other reasons.

There is therefore an additional need to ensure a reliable sensed signal from a probe, integrated into a garment, requiring at least some compensation for both an initial misplacement and physical activity displacement.

It should be noted that such a mechanism can be useful in any system with sensors and probes that may move away from their optimal location, thus degrading the quality of their measurement.

BRIEF SUMMARY OF THE INVENTION

The principal intentions of the present invention include providing a health monitoring and self-alert system, for detecting one or more potentially health hazardous situations. The health monitoring and self-alert system is in the form of a wearable underwear items/garments that provides a personal health alert, upon detecting an abnormal health situation, preferably provided on a mobile device having a processor, such as a regular mobile/smart-phone, tablet, mobile computer etc., herein denoted, with no limitation as "smartphone". Optionally, a personal-alert function is also part of the wearable device, integrated into the wearable underwear items/garments, independent of any carried mobile device.

The system of the present invention facilitates measuring health related bodily parameters, preferably including measuring clinical level ECG, analyzing the data in real-time, and upon detecting a situation which requires further investigation or immediate intervention, alarms the system carrier to seek medical help. Analogously, the innovative system replaces the family doctor or substantially any other professional physician, who would have, seeing the abnormal measured parameters, sent the person to the Emergency room. Hence, analogously, the innovative system substantially reduces the need to consult with a family doctor, on a 24/7 basis in acute cases. Furthermore, it acts like a seamless family doctor that advises the user when it is an acute case needing a hospital investigation or intervention, even when the user is not aware of the situation.

According to the teachings of the present invention, there is provided a seamless, substantially continuous, independent and wearable health monitoring and self-alert system, configured for use by a living being on a daily basis, including by a healthy living being. The wearable health monitoring and self-alert system includes a garment worn by the living being adjacently to preconfigured portions of the body of the living being. The system further includes a garment-control device that includes a garment-processor and a battery. The system further includes a multi-lead ECG measuring device including multiple electrodes or probe-devices, and an alerting unit.

Optionally, the garment-processor and the battery are operatively disposed in a designated pocket in the monitoring-garment, wherein the garment-processor and the battery are removably connected to a respective designated button. Optionally, the garment-processor is automatically activated when operatively connecting to the battery to reduce required user's actions.

Preferably, the power source is a rechargeable battery whereas the charging should require no special care/operation by the user. For example, the charger is shaped or built into a closet hanger. Optionally, the charger is a charging plate. Preferably, the energy harvesting module is integrated into the undershirt to thereby facilitate recharging while in operation (e.g. by regular movements of the carrier). Optionally, a removal of the battery facilitates recharging the battery without having to attach the charging device to the monitoring-garment. In some variations of the current invention, the recharging may be done without removing the battery from the monitoring-garment, for example, by using a cable between the recharger and the battery (using a USB connector or any other connector) or by wireless techniques (charging plate, charging hanger etc.).

The multiple electrodes of the multi-lead ECG measuring device are embedded into the garment and configured to detect continuous cardiac electrical activity. The garment-processor is integrated in the garment and is in operational communication flow with the multi-lead ECG measuring device. The lead-wires that connect the electrodes and sensors to the processing unit device are preferably seamlessly knitted into the monitoring-garment in the production phase of the monitoring-garment (for example, by using a Santoni knitting machine), and preferably include some protecting coating. This way the monitoring-garment is seamless and facilitates regular laundry washing.

The electrodes are typically made of washable conductive yarn. The exact place of each electrode is part of a preconfigured design of each type of monitoring-garment, planned to cover the ECG points (and other points in case of other types of sensors) on the body. The electrodes may vary in size and shape as part of a specific design, providing some flexibility for the slight movements of the garment when wearing and moving.

The garment-processor analyzes the detected continuous cardiac electrical activity, to thereby determine if one or more ECG-parameters of the detected continuous cardiac electrical activity, or a combination of the ECG-parameters, are abnormal. When at least one of the ECG-parameters or a combination thereof, is determined to be abnormal, the alerting unit is operatively activated by the garment-processor to issue a personal-alert to the living being carrying the health monitoring and self-alert system, in real time.

Optionally, the health monitoring and self-alert system further includes multiple sensing devices selected from the group consisting of sensors and electrodes. At least one of the sensing devices is embedded into the garment, wherein each of the sensing devices is configured to detect a predetermined physiological or chemical parameter of the living being. The garment-processor is integrated in the garment and is in operational communication flow with the sensing devices. Preferably, the sensors are embedded in such a way that the sensors are unseen by other people and not felt by the user to thereby comply with the "seamless" requirement.

Preferably, the garment-control device further includes a remote-processor and a transmitter, wherein the remote-processor is built into a personal mobile device, such as a smart-phone, coupled with the living being. The personal mobile device is typically held by the monitored person or is near the person being monitored. The garment-processor is facilitated to receive the ECG-parameters and/or the detected parameters and transmit the received parameters by the transmitter to the remote-processor, wherein the analysis of the detected parameters is performed by the garment-processor, the remote-processor or a combination thereof. When at least one of the received parameters or a combination thereof, is determined to be abnormal, the activation of the alerting unit is performed by the remote-processor.

Optionally, when the living being is an animal, the mobile computing device is coupled with the caretaker of the animal.

Preferably, the multi-lead ECG measuring device includes at least twelve electrodes, to thereby facilitate clinical level ECG measurements clinical level cardiologic ischemia analysis. Preferably, the multi-lead ECG measuring device including at least fifteen electrodes, to thereby improve the measurements sensitivity, wherein the clinical level cardiologic ischemia analysis facilitates detecting health abnormalities selected from the group including ST elevation, ST depression, T-wave inversion and new left bundle branch block.

Preferably, one or more of the sensing devices are accelerometers, configured to detect motion and posture position of the living being, wherein the clinical level cardiologic ischemia analysis includes body motion & posture compensations, to thereby facilitate the personal-alert to be issued either in rest or in active states of the living being.

Optionally, personal-alert are subdivided into alert levels, wherein the sensing alert levels include a yellow alert level, advising the living being to seek medical advice, and a red alert level, urging the living being to seek immediate medical help.

Optionally, one or more of the sensing devices and/or the probe devices include a multiplicity of substantially identical sensors or electrodes, and a probe processor; wherein the identical sensors or electrodes are configured to sense the same physiological or chemical parameter of the living being; wherein the probe processor is preconfigured to select a best sensed-signal out of the signals provided by the identical sensors or electrodes; wherein the best sensed-signal is selected according to a pre-configured selection-methodology; and wherein the best sensed-signal is transmitted to the garment-processor.

Optionally, the selection-methodology includes selecting the signal being the strongest, having the best SNR or a combination thereof.

Optionally, the selection-methodology includes selecting the signal best matches a predetermined "normal" signal, wherein the "normal" may be the average normal signal of living beings of the same species of the particular living being; the average normal signal of living beings of the same gender of the particular living being; the average normal signal of living beings of the same age group of the particular living being; a value set by the physician of the particular living being, or a combination thereof.

Optionally, the multiple sensing devices include respiration detecting sensors to thereby detect respiration abnormalities, wherein preferably, the respiration abnormalities include Sleep Apnea and Dyspnea.

Optionally, the boundary definition of the parameter abnormality is personally, dynamically and automatically adapted to the changes over time of the normal state of the living being. Optionally, the operation of the system requires no operative action to be performed by the living being, before or during the health monitoring.

Optionally, the remote processor has an optional adaptation algorithm that determines the "normal state" of the monitored person, so that the thresholds and other parameters' characteristics may be individually set, preferably automatically. Furthermore, the adaptation mechanism is substantially continuously active, so that the dynamic nature of the human state is taken into account in the adaptation process. Furthermore, the processor can determine the ergonomic parameters and physical status of the monitored living being (standing, sitting, lying down, extreme activity etc.), using motion-posture algorithms based on sensors such as accelerometer and gyro based detectors controlled by the system control unit. The motion-posture algorithms are used to improve the accuracy of the abnormalities detected, by taking into account the motion/posture of the monitored person Preferably, the mobile device, having a display, includes a calibration application, performed by the remote-processor, including the steps of displaying a garment-body illustration of the garment-body, and activating each of the sensing devices. Each of the sensing devices analyzes the signal of the sensor, determines the quality of the signal and displays a go/no-go indication for the signal.

Optionally, the monitoring-garment includes a controlled adjustable tightening-mechanism, facilitating manual tightening of special wires/threads in specific regions of the monitoring-garment, when a specific sensor requires better contact with the body of the living being. Optionally, the adjustable tightening-mechanism includes contractible threads operatively controlled by the garment-processor. In response to sensed data received from the specific sensor, the garment-processor activates, for example, an external knitting system, to thereby adjust the length of the special tightening wires/threads.

In the fitting process, the smart-phone application provides instructions and confirmation about the right size choice, or the specific portions of the monitoring-garment that are not tight enough, based on the quality of signals from the various sensors. The instructions and confirmations are intended to be used also in the regular daily wearing procedure of the wearable device by the user (e.g. alert when one of the sensors is not placed tight enough) and during the continuous wearing of the monitoring-garment.

The monitoring-garment is designed with versions adapted for use by male or female persons, day and night, for regular or special (e.g. sport) usage, wherein the various sensors of the system are embedded in the monitoring-garment. It should be noted that any wearable clothing may be used, as long as the wearable clothing has a direct and preferably tightened contact with the skin of the person in the appropriate designated area as required by each of the sensors. It should be noted that some sensors do not require the abovementioned direct contact for example, accelerometers and breathing sensors. In the case of direct contact, the various sensors and electrodes are preferably dry, i.e. do not require any jell or other connecting materials to be placed on the body before and while wearing the monitoring-garment. Moreover, the placement of the sensors and/or electrodes, with respect to the user's body, does not require any professional (physician, nurse etc.) help or even any third party help; the normal wearing operation is adequate for the satisfactory placement of every component embedded in the monitoring-garment.

An aspect of the present invention is to provide a probe device for configured detecting a predetermined physiological or chemical parameter of a particular living being, including a moving living being. The probe device includes a multiplicity of substantially identical sensors or electrodes, a probe processor and a communication line, wherein the identical sensors or electrodes are configured to sense the same physiological or chemical parameter of the particular living being.

The probe processor is preconfigured to select a best sensed-signal out of the signals provided by the identical sensors or electrodes, wherein the best sensed-signal is selected according to a pre-configured selection-methodology, and wherein the best sensed-signal is transmitted to predetermined target recipient.

An aspect of the present invention is to provide a method for monitoring the health status of a living being and issuing a personal-alert upon detecting a potentially health hazardous situation. The method includes the steps of:

a) providing a seamless independent wearable health monitoring and self-alert system including a monitoring-garment, worn by the living being adjacently to preconfigured portions of the body of the living being, having a garment-processor, a remote-processor, a transmitter and an alerting unit;

b) sensing designated health related parameter by the sensors, thereby obtaining sensed data;

c) analyzing the sensed by the garment-processor, to thereby create analyzed sensed data;

d) determining if the analyzed sensed data is abnormal;

e) if the analyzed sensed data is determined to be abnormal, transmitting the analyzed sensed data to the remote-processor; and f) activating the alert unit by the remote-processor to thereby issue a personal-alert to the living being, in real time.

Preferably, the determining if the analyzed sensed data is abnormal includes considering the current motion-posture state of the living being.

Preferably, the determining if the analyzed sensed data is abnormal includes considering respective threshold values, the number of leads, the number of contiguous leads or a combination thereof.

Optionally, the remote-processor further analyzes the analyzed sensed data, to thereby determine if to issue a personal-alert.

Optionally, the remote-processor further includes the step of determining the level of the personal-alert.

Optionally, the determining the level of the personal-alert is determined based on a single health related event, multiple health related events, health related patterns or a combination thereof.

Optionally, the single health related event includes biasing data selected from the group including: degree of abnormality, motion and posture considerations, temporary treatment effects, activity effects and confidence level.

Optionally, the multiple health related events, health related patterns include biasing data selected from the group including: first or repeated event, number of abnormal parameters in one measuring interval, repeated known pattern, new pattern, consistency and confidence level.

Preferably, the determining the level of the personal-alert is determined based on personal data pre-entered by a professional person, acquainted with the living being. The remote processor has a "doctor's instructions" module, that enables a physician to insert specific instructions, thresholds, rate of events patterns, cross-checking (with motion/posture state, for example), trend comparisons an other considerations, to facilitate an alert that is substantially similar to a professional physician's decision about the need for further investigation.

In variations of the present invention, the definition of the abnormality of the physiological or chemical parameter may be personally adaptive and dependent on "Doctor's Instructions" input regarding the specific conditions suited for the specific user. In variations of the present invention, the definition of the abnormality is dynamically adaptable per the changing state over time of the user and optionally, influenced by the motion-posture status.

An aspect of the present invention is to provide a method for preliminarily analyzing and sorting-out sensed data obtained by multiple sensors. The method includes the steps of:

a) providing a seamless independent wearable health monitoring and self-alert system including a monitoring-garment, worn by the living being adjacently to preconfigured portions of the body of the living being, having a garment-processor, and multiple sensing devices selected from the group consisting of sensors and electrodes.

b) activating the sensors, by the garment-processor, in cycles having a preconfigured sequence and time interval, wherein each cycle includes the steps of:
  i. selecting next sensor$_i$;
  ii. obtaining sensed data from sensor$_i$;
  iii. determining if the sensed data is abnormal; and
  iv. if the sensed data is determined to be abnormal, transmitting the sensed data to a preconfigured target receiver.

The alert is a personal-alert, and is preferably issued to the person wearing the system, regardless of the location (indoors and outdoors), at rest or in any dynamic movement (e.g. running, skiing, bicycling . . . ) with many optional and preferably, selectable ways to issue the alert (e.g. ringtone, voice, SMS). The alert may also be sent to other preconfigured receiving entities (e.g. other people, remote monitoring center). Some of the data may be displayed on the display of the smart-phone or the other devices (e.g. the ECG signal, the heart-rate fluctuations) in addition to the alert. Optionally, the processing unit device integrated into the monitoring-garment may include a special display (LCD or other) for displaying processed data. Optionally, the processing unit device integrated into the monitoring-garment facilitates operationally connected to an external computerized device for maintenance purposes.

Preferably, an automatically adaptive threshold, for one or more selected parameters or combination of parameters or a trend that is hazardous in the future, for that person, and medical treatment may be used in the alert issuing decision making.

The person wearing the monitoring-garment is not limited in any way, in his or her regular lifestyle, and does not have to adjust or perform any special activity in order to eventually get the alert when needed. Preferably, no signs are observable that the person is using a monitoring and alert system and the embedded sensors are not felt by the user, thus, the system is fully seamless.

The monitoring-garment is preferably washable in regular washing-machines thus facilitating the reusability of the system. Optionally, preconfigured components of the processing unit device (e.g. processor, Bluetooth transmitter, accelerometers and rechargeable battery) are configured as removable units. The removing and reattachment are very easy, preferably by a one-click operation. This removal facilitates repeated washing of the monitoring-garment.

Optionally, the remote processor analyzes and determines correlation between the detected parameters of two or more of the detected sources of data, thereby creating correlated parameters (for example, ECG and respiration). When the detected correlated parameters are determined to be abnormal, other aspects of the situation are analyzed, such as: past events, trends, known characteristics of the user, special instructions regarding the conditions when a personal-alert should be issued (typically originated by a physician knowing the specific user medical behavior). Accordingly, the alerting unit is operatively activated to alert one or more predetermined alert receiving entities. Preferably, the system is facilitated to provide the alert with no operative action performed by the user during health monitoring. These functionalities may reside, partially or fully at the mobile device.

BRIEF DESCRIPTION OF THE DRAWINGS

The present invention will become fully understood from the de ailed description given herein below and the accompanying drawings, which are given by way of illustration and example only and thus not limitative of the present invention:

FIG. 2a is a schematic illustration of the undershirt shown in FIG. 1, showing a removable garment-processor and a removable battery of the garment-control device;

FIG. 2b is a detailed view illustration of window A, shown in FIG. 2a;

DETAILED DESCRIPTION OF THE INVENTION

Figure 1:
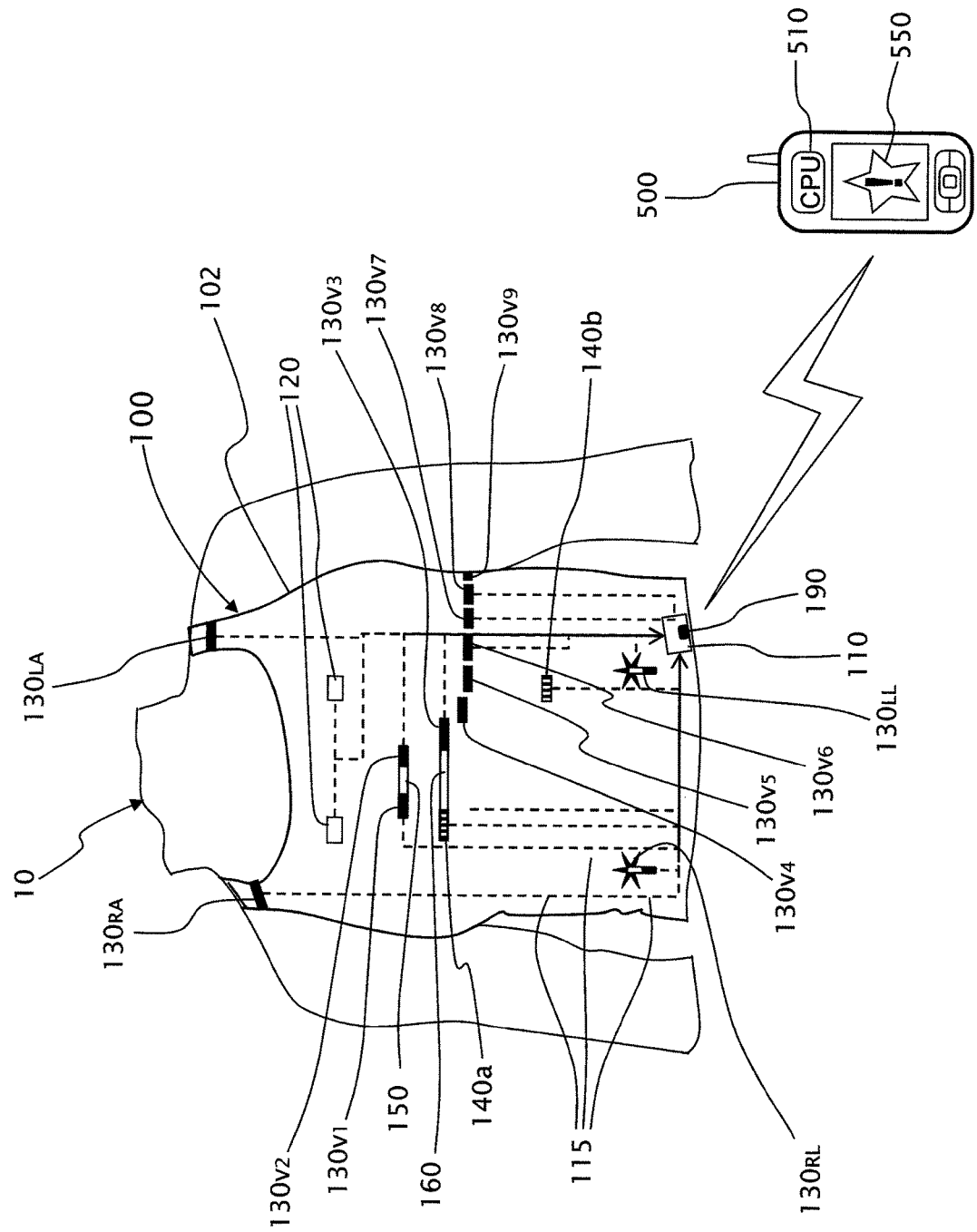
FIG. 1 schematically illustrates a seamless independent wearable health monitoring and self-alert system, including an undershirt, being an exemplary underwear monitoring-garment, according to embodiments of the present invention, wherein interconnected sensors, a garment-control device and a mobile device, having a remote-processor.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques and procedures either known to, or readily developed from known manners, means, techniques and procedures by practitioners of the art to which the invention belongs. The descriptions, examples, methods and materials presented in the claims and the specification are not to be construed as limiting but rather as illustrative only.

Meanings of technical and scientific terms used herein are to be commonly understood as to which the invention belongs, unless otherwise defined. The present invention can be implemented in the testing or practice with methods and materials equivalent or similar to those described herein.

It should be noted that the present invention will often be described in terms of the monitoring-garment being an undershirt, but the present invention is not limited to an undershirt being the monitoring-garment, and type of garment, at least partially worn adjacently to the body of the monitored living being can be used as a monitoring-garment.

It should be noted that the present invention will be described in terms of the mobile device being a smart-phone, but the mobile device of present invention is not limited to being a smart-phone, and includes all types of mobile devices having a central processing unit and memory, including a mobile phone, laptop, a PDA, a processing pad, etc., all having Bluetooth or any other wireless communication capabilities. According to the teachings of the present invention, there is provided an independent, seamless and preferably substantially continuous health monitoring system, designed for use by a healthy living being but also suitable for non-healthy living being.

Figure 2:
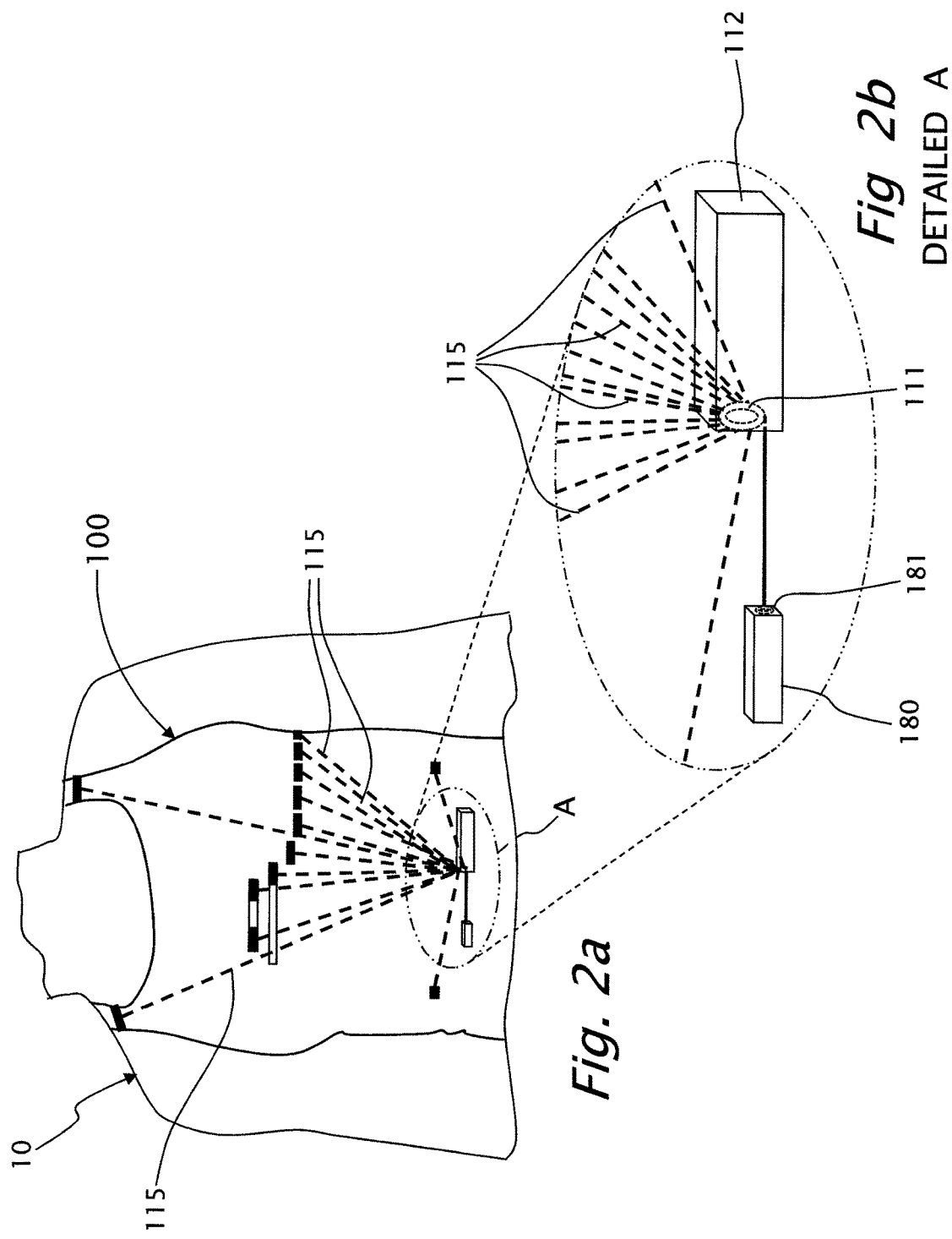

Reference now made to the drawings. FIG. 1 schematically illustrates a seamless, independent, wearable and preferably continuous health monitoring and self-alert system, including an undershirt 100 and a preferably mobile device 500, having a remote-processor 510, according to embodiments of the present invention, wherein using mobile device 500 is a preferable option. FIG. 2a illustrates an undershirt monitoring-garment 100, showing a removable garment-processor and a removable battery of the garment-control device. Undershirt 100 is a non-limiting, exemplary monitoring-garment item, wherein interconnected sensors 120, 130, 140, 150 and 160, and a garment-control device 110, are schematically illustrated in FIG. 1. Sensors 120, 130, 140, 150 and 160 are embedded into the garment-body 102 of monitoring-garment 100.

Typically, undershirt 100 looks like a regular undershirt and preferably, the embedded sensors (120, 130, 140, 150 and 160, and possibly other sensor types) are not seen from the outside and not felt by person 10. A person 10 can easily wear the undershirt in any situation where he or she is used to. When the undershirt is firstly provided to person 10, the size and tightness to the person's body are adjusted such that the sensors (120, 130, 140, 150 and 160) are at the correct bodily regional places and with appropriate contact with the person's body. In this fitting process, the smart-phone and/or a garment-control device 110 application, provides instructions and confirmation about the right size and positioning choice.

Garment-body 102 of monitoring-garment 100 is preconfigured for wear by either a man or a woman and preferably comes in a variety of sizes. Garment-body 102 is typically made of elastic, non-sweating materials and is preferably tight-fitted to the designated body portions of monitored person 10, for receiving appropriate signals with an adequate quality. The sensors (120, 130, 140, 150 and 160) are embedded into garment-body 102 of monitoring-garment 100 such that when monitoring-garment 100 is worn, the sensors (120, 130, 140, 150 and 160) are preferably tightened to the skin of the monitored person 10 at a respective, preconfigured position, per each sensor's specific functionality.

Preferably, also embedded into garment-body 102 of monitoring-garment 100 are wires interconnecting some of the sensors (e.g. between couples of impedance sensors 150). Also embedded into garment-body 102 of undershirt 100 are wires connecting all of the sensors (120, 130, 140, 150 and 160). Optionally, also embedded in the monitoring-garment, are wires interconnecting some of the sensors (e.g. between couples of impedance sensors 150).

Figure 3:
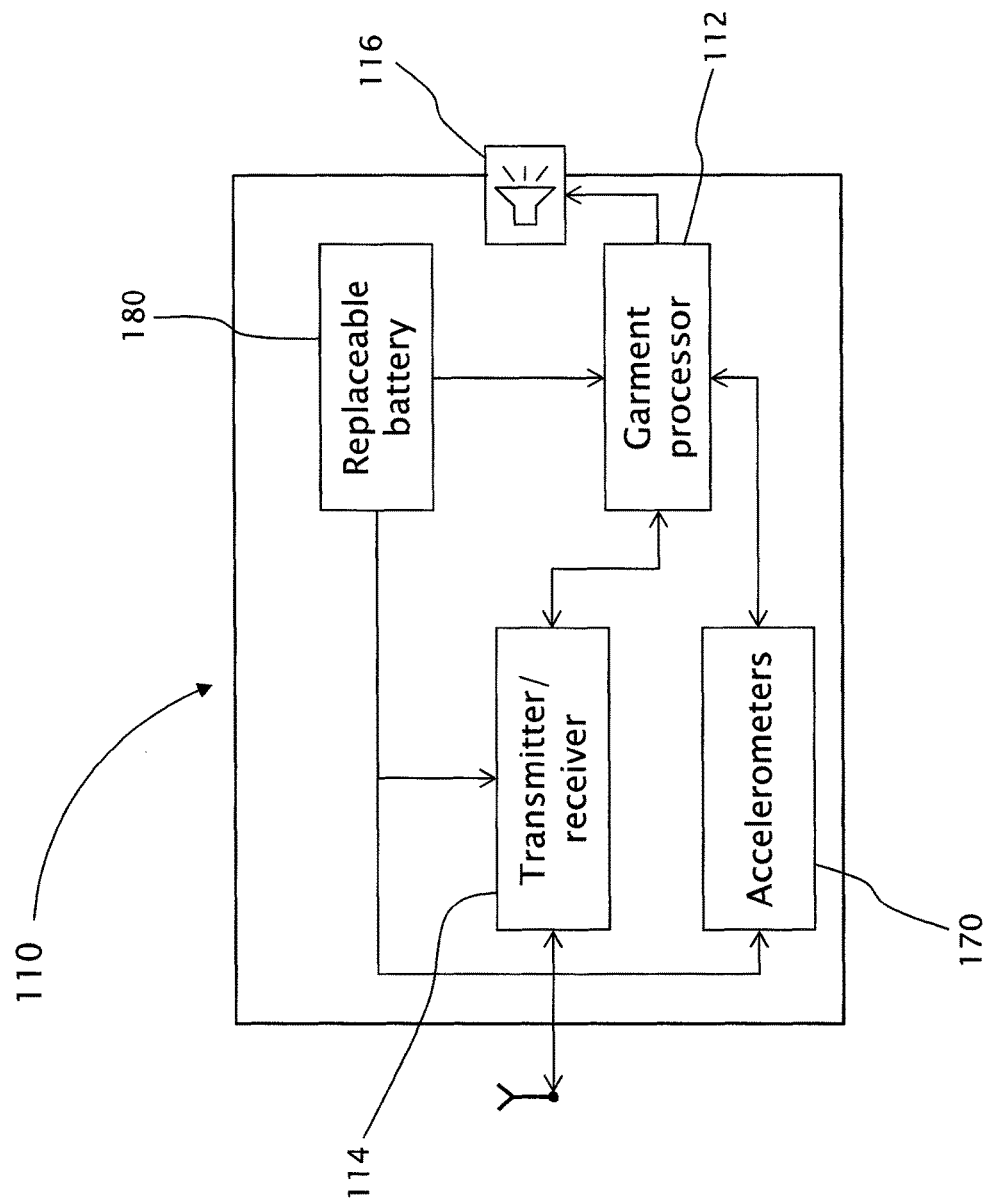
FIG. 3 is a schematic block diagram of one embodiment of the garment-control device shown in FIG. 2b.

Reference is also made to FIG. 2b, a detailed view illustration of a window A, as shown in FIG. 2a; and to FIG. 3, a schematic block diagram of one embodiment of garment-control device 110. Also embedded into garment-body 102 of undershirt 100 is garment-control device 110, wherein wires 115 interconnect all of the sensors (120, 130, 140, 150 and 160) to garment-control device 110, preferably by wires 115 knitted into monitoring-garment 100. Garment-control device 110 includes a garment-processor 112 and a preferably rechargeable battery 180, wherein garment-processor 112 and battery 180 are preferably removable. Preferably, garment-control device 110 further includes a transmitter 114, typically short range transmitter such as Bluetooth, facilitating wireless communication between garment-processor 112 and remote-processor 510 of mobile device 500. Optionally, garment-control device 110 further includes an alerting unit 116.

In one embodiment of the present invention, garment-control device 110 preferably transmits the sensed data, as provided by the sensors (120, 130, 140, 150 and 160), to remote-processor 510 of mobile device 500, via transmitter 114. In other embodiments of the present invention, garment-processor 112 analyzes the sensed data obtained by one or more of the sensors (120, 130, 140, 150 and 160) and prevents sensed data that is well within a preconfigured range of normal parameter, from being transmitted by transmitter 114 to remote-processor 510. Thereby, substantially reducing the transmittal time and saving in transmittal power.

The embedded garment-processor 112 has a filtering function to substantially limit the transmissions to the mobile device. One part of that function is limiting the transmission, when there are no problems detected and selecting only the suspected abnormal data to be transmitted. This function significantly reduces the amount of energy needed, thus preserving the battery power. In addition, the algorithms determine the sensing rate: while in normal state the rate may be low, when sensed data is closer to abnormality values, the sensing and transmission rates are higher.

In some embodiments of the present invention, garment-processor 112 analyzes the sensed data obtained by one or more of the sensors (120, 130, 140, 150 and 160) to thereby determine if a health hazardous situation has occurred. In such an event, garment-processor 112 activates an alerting unit 116, coupled to operate with garment-processor 112, to thereby provide a personal-alert to person 10. The personal-alert may be in the form of an audio sound, a light indication, any other form known in the art, or a combination thereof.

Garment-processor 112 may further calculate values, compare thresholds, trends, averages etc., and may provide the calculated data to an external recipient. Preferably, garment-processor 112 further includes memory for storing data for calculations, comparisons to past measurements, determining trends, calibration, determining sensors reliability, further remote analysis at external places and for future use (for example, for use in physical exercise consulting).

In some embodiments of the present invention, garment-control device 110 is subdivided into multiple, individual processing units, wherein each of the individual processing unit is operatively coupled with one or more sensors.

Reference is made back to FIG. 2b. Optionally, garment-processor 112 and battery 180 are operatively disposed in a respective designated pocket in monitoring-garment 100, wherein garment-processor 112 and battery 180 are removably connected to a designated button 111 and 181, respectively, wherein optionally, buttons 111 and/or 181 facilitates one-click connection or removal operations.

Optionally, garment-processor 112 does not have an "On/Off" button, but its activation automatically when inserted into the "one-click" button. This eliminates the need of a manual activation by the user, which is a source for errors and inconvenience.

In the example shown in FIG. 1, sensors 120 represent optical sensors for sensing the oxygen level in the blood. ECG sensors 130 are for detecting heart-rate (FIR) related irregularities (arrhythmia) as well as ischemia (more precisely, placed at the standard ECG positions), facilitated by a 12-lead ECG or more. Acoustic sensors 140 are for detecting lung fluids and HR and impedance sensors 150 are for detecting congestive heart failure (CHF). Also breathing sensors, such as carbon-elastomer stretch or impedance sensors that can detect breathing rhythm and breathing regularity or irregularity. A pressure sensor 160 is an example sensor that measures the in and out motion of the thorax, facilitating detecting breathing and measuring breathing rate. The sensors may further include sweat analysis sensors, temperature and other sensors.

To facilitate clinical level ECG measurements and thereby clinical level cardiologic ischemia analysis, ECG sensors 130 may include a multiple-lead ECG, preferably, with 12-lead, optionally with more leads, such as a 15-lead ECG, as shown in FIGS. 1 and 2a, having additional electrodes on the back (such as at positions $V_7$, $V_8$) and on the left side of person 10. In embodiments of the present invention, the only sensors that the health monitoring and self-alert system includes are multiple-lead ECG (multi-lead ECG), facilitating clinical level ECG measurements and thereby clinical level cardiologic ischemia analysis. The ECG can thus be a 15-lead ECG (for added sensitivity), an 18-lead ECG or any additional number of electrodes that the wearable platform enables. The sensors are embedded in the monitoring-garment so that they are tightened to the skin at a respective preconfigured position, per each sensor's specific functionality (e.g. ECG—standard positions, acoustic—at the basal aspects of the lungs).

The ECG can detect, for example, heart-rate (HR) related irregularities as well as ischemia (for example, ST elevation and depression, T-wave inversion and new left bundle branch block). Blood pressure is also indicative of heart or other cardio-vascular problems, as well as body temperature changes.

Optionally, sensors may be integrated into a single unit. For example, in FIG. 1, electrodes $130_{v1}$ and $130_{v2}$ are integrated with an impedance sensor 150; and an electrode $130_{v3}$ is integrated with an acoustic sensor 140 and a pressure sensor 160.

As indicated hereabove, the health monitoring and self-alert system of the present invention preferably includes a mobile device 500, having a remote-processor 510. Remote-processor 510 receives sensed data from monitoring-garment 100, preferably, at least partially processed, further analyzes the received data, as needed, and determines if a health hazardous situation, that justifies the issuing of a personal-alert has occurred. In such an event, remote-processor 510 activates an alarm indicator 116, coupled to operate with remote-processor 510, to thereby alarm person 10 with a personal-alert 550. The personal alert may be in the form of an audio sound, a video image, an SMS, or any other form known in the art, or a combination thereof.

It should be noted that typically, a personal-alert is issued by the remote mobile processor 510. The configuration of the health monitoring and self-alert system, where garment-control device 110 issues a personal-alert, is typically used as a backup mode.

Remote-processor 510 may further calculate values, compare thresholds, trends, averages etc, and may provide the calculated data and/or raw data to an external recipient. Preferably, remote-processor 510 further includes memory for storing data for calculations, comparisons to past measurements, determining trends, calibration, determining sensors reliability, further remote analysis at external places and for future use (for example, for use in physical exercise consulting).

An aspect of the present invention includes providing a method for controlling the multiplicity of sensors embedded in a monitoring garment 100. The multiplicity of sensors is activated in a preconfigured sequence, which sequence may be dynamically adapted to the health status of the monitored person 10. For example, when a sensor detects sensed data that is nearly out of normal range or is slightly out of normal range, the sensing frequency of that sensor, and possibly other related sensors, is increased.

Figure 4:
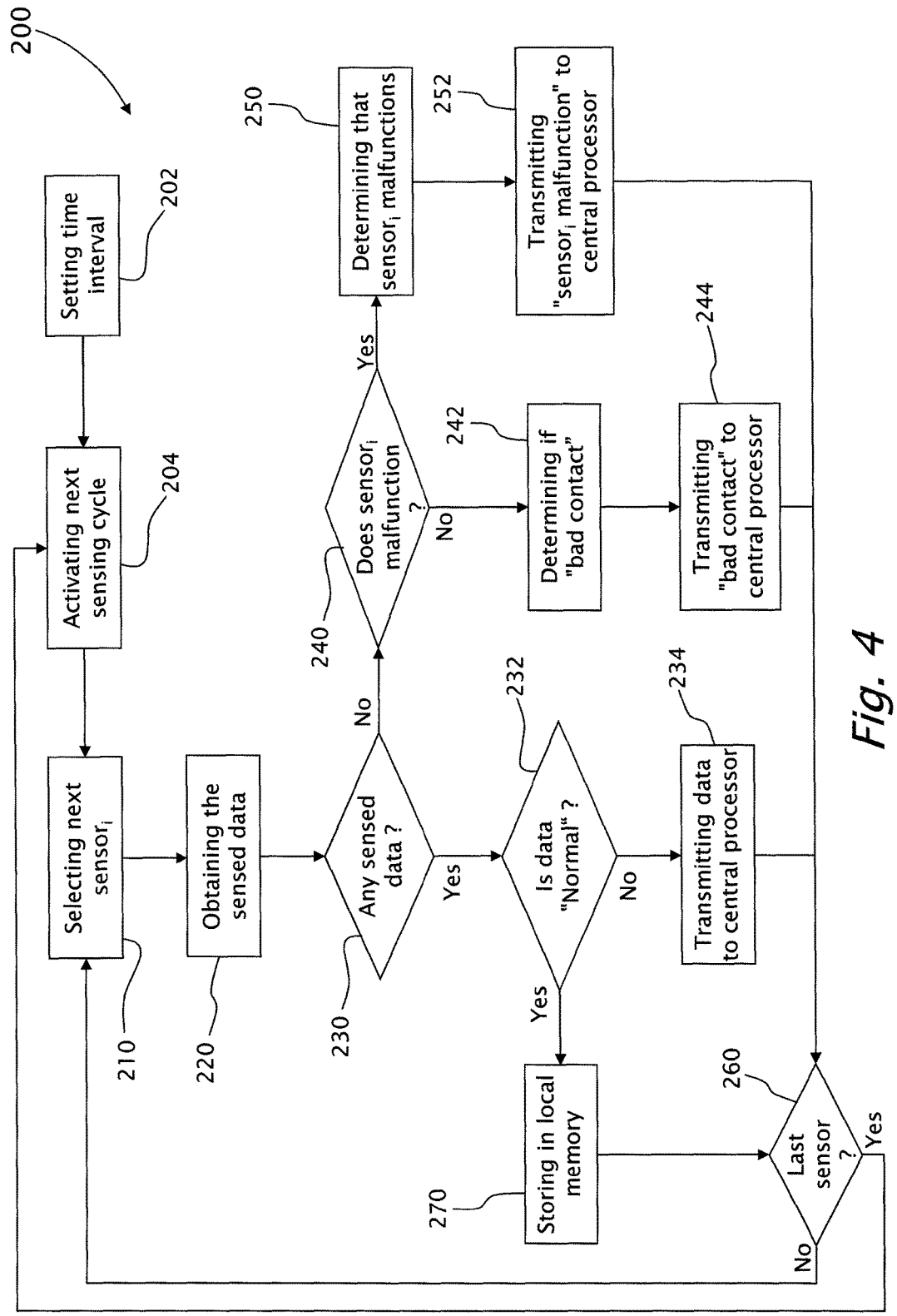
FIG. 4 is a schematic flow diagram that outlines the steps of an exemplary cyclic sensing method, performed by a garment-control device embedded in the monitoring-garment, and the steps of preliminarily analyzing and sorting-out the sensed data as to whether to transmit the sensed data to the remote-processor.

Reference is made to FIG. 4, which is a schematic flow diagram 200 that outlines the steps of an exemplary cyclic sensing method, preferably performed by garment-control device 110 of monitoring garment 100, and the steps of preliminarily analyzing and sorting-out the sensed data. Method 200 is described, by way of example only, with no limitation, in a system including a monitoring garment 100 and a smart mobile device 500.

Method 200 begins by setting the sequence and time intervals between cycles and between sensors of activating the multiplicity of sensors embedded in underwear 100 (step 202). Upon arrival of the next sensing cycle time interval, the next sensing cycle is activated (step 204). Method 200 proceeds with the following steps:

Step 210: selecting next sensor$_i$.
Each sensor$_i$ (120, 130, 140, 150 or 160) is activated, according to the currently configured sequential order, to thereby sense the parameter that sensor$_i$ is preconfigured to measure.

Step 220: obtaining sensed data from sensor$_i$.
The sensed data is obtained by garment-control device 110.

Step 230: garment-control device 110 analyzes the sensed data.
Garment-control device 110 determines if the sensed data is null.
If the sensed data is null, go to step 240.

Step 232: determining if the sensed data is "Normal".
Garment-control device 110 determines if the sensed data is "normal".
If the sensed data is "normal", go to step 270.

Step 234: transmitting the sensed data to remote-processor 510.
The sensed data is suspected to be out of "normal range" and thereby transmitted to remote-processor 510 for final analysis.
Go to step 260.

Step 240: determining if sensor$_i$ malfunctions.
Garment-control device 110 determines if sensor$_i$ malfunctions or simply read no data due to dislocation.
If sensor$_i$ malfunctions, go to step 250.

Step 242: determining if "bad contact".
Garment-control device 110 determines that the sensed data is null because of "bad contact".

Step 244: transmitting "bad contact" to remote-processor 510.
Garment-control device 110 transmits "bad contact" for sensor$_i$, to remote-processor 510.
Go to step 260.

Step 250: Determining that sensor$_i$ malfunctions.
Garment-control device 110 determines that sensor$_i$ malfunctions.

Step 252: transmitting "bad contact" to remote-processor 510.
Garment-control device 110 transmits "bad contact" for sensor$_i$, to remote-processor 510.

Step 260: determining if sensor$_i$ is the last sensor of the sequence of sensors.
If sensor$_i$ is not the last sensor of the sequence of sensors, go to step 210.
Else, go to step 204.

Step 270: storing in local memory.
Garment-control device 110 determined that the sensed data is "normal". Preferably, garment-control device 110 stores the "normal" sensed data in a designated local memory, preferably, a non-volatile memory.
Go to step 260.

(end of steps details of cyclic process 200)

In variations of the present invention, the definition of the abnormality of the physiological or chemical parameter is personally adaptive, wherein the "normal" health state of a particular monitored living being is personally set. In variations of the present invention, the definition of the abnormality is dynamically adaptable per the changing state over time of the living being.

Upon detecting abnormal health related parameters, or an abnormal state determined as a result from an analysis of combined inputs acquired from different sensors, or from a trends analysis, remote-processor 510 sends a personal-alert through smart-phone 500. Optionally or additionally, remote-processor 510 sends personal-alert information to a predetermined external recipient. Optionally, remote-processor 510 analyzes and determines the correlation between the detected parameters of two or more of the detected, thereby creating correlated parameters. When the detected correlated parameters are determined to be abnormal, the alerting unit is operatively activated to alert one or more predetermined alert receiving entities.

There may be various types of personal alerts, such as the following non limiting examples: audio (ringtone, voice, etc.), visual (SMS, screen display, etc.) and digital signals designated for various target recipients.

In variations of the present invention, sensors are selected from the group of physical sensors including an electric sensor, an optical sensor, an acceleration sensor (usually an accelerometer for each of the three dimensions), a blood pressure sensor, an oximeter (e.g. reflectance oximeter), pressure impedance sensors optionally with 4 electrodes, a conductivity sensor, a temperature sensor, breathing sensors, a humidity (sweat) sensor and other sensors.

It should be further noted that some of the processing tasks may be performed at a remote monitoring center. The garment-processor 112 or mobile device 500 may send the data (sensed data or at least partially analyzed sensed data) to any remote processor, which can further process the information, compare the obtained data to corresponding data obtained from other monitored people, make statistics-based decisions and other decision-making issues to improve alerts sensitivity and specificity (for example by detecting suspicious trends that did not trigger the automatic alert but a physician may want to further check the person) and providing information for assisting the treatment of the living being once getting to a treating facility.

Preferably, the health monitoring and self-alert system includes sensors for detecting the characteristics of the physical activities and posture of the living being, for example, acceleration sensors 170 (see FIG. 3), pressure sensors, orientation sensors, etc. Acceleration sensors 170 may be integrated within garment processor 110, or at other preconfigured locations in garment-body 102.

An aspect of the present invention includes providing a method for monitoring the health status of a living being and issuing a personal-alert upon detecting a potentially health hazardous situation.

Figure 5:
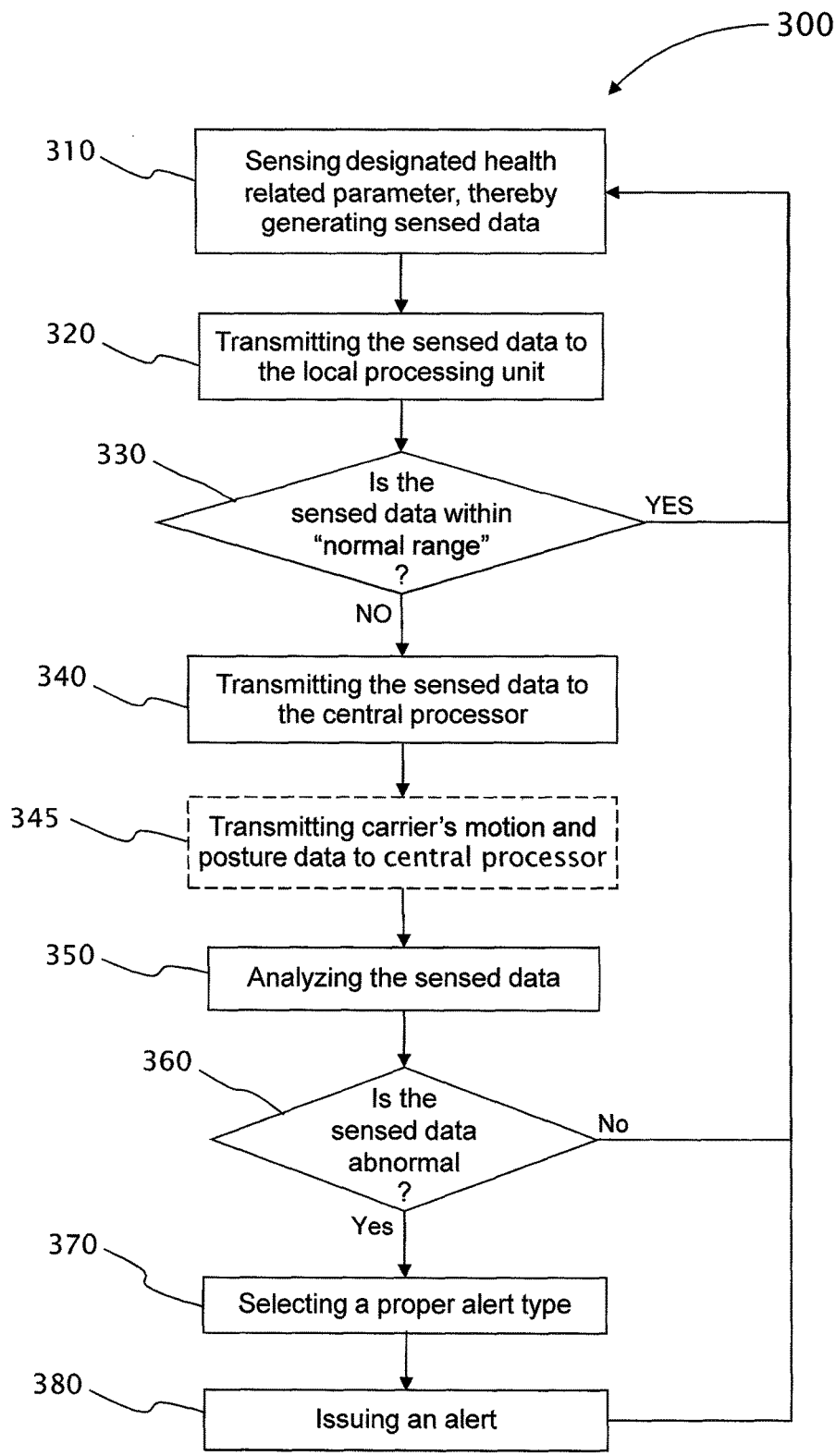
FIG. 5 is a schematic flow diagram that outlines the steps of monitoring the health status of a living being, performed for example on the system shown in FIG. 1, and the steps of activating an alerting unit upon detecting a potentially health hazardous situation.

Reference is made to FIG. 5, which is a schematic flow diagram 300 that outlines the steps of monitoring the health status of a living being 10, performed for example on a system combining monitoring garment 100 and mobile device 500, and the steps leading to issuing a personal-alert upon detecting a potentially health hazardous situation. Method 300 includes the following steps:

Step 310: sensing designated health related parameter, thereby generating sensed data.
  Each sensor$_i$ (120, 130, 140, 150 or 160) senses the parameter that sensor$_i$ is preconfigured to measure, and thereby generating sensed data. For example, sensor$_i$ is an acoustic sensor 140 preconfigured to detect lung fluids. Hence, in this example, the sensed data is the measured level of acoustic noise.
Step 320: transmitting the sensed data to garment-control device 110.
  The sensed data is preferably transmitted to garment-control device 110 for initial analysis. To continue the example, the measured level of acoustic noise coming from the lung is transmitted to garment-control device 110.
Step 330: garment-control device 110 analyzes the sensed data.
  Garment-control device 110 analyzes the sensed data to thereby determine if the sensed data is in normal range.
  If the sensed data is within the normal range, go to step 310.
  It should be noted that a preliminary step of determining the "normal range" ("normal range" being non-abnormal range) for a specific individual (function of parameters like age, family history, life style etc.) and a specific ergometric state (such as standing, lying, extreme effort, etc.) is optionally performed. Optionally, the parameters and coefficients are remotely set up and/or controlled.
Step 340: transmitting the sensed data to remote-processor 510.
  The sensed data is transmitted to remote-processor 510 for a final analysis. To continue the example, the measured level of acoustic noise coming from the lung is transmitted to remote-processor 510.
Step 345: transmitting carrier's motion and posture data to remote-processor 510.
  Optionally, the sensed motion and posture data is transmitted to remote-processor 510. For example, movement related data can be running jumping, exerting physical force, etc.; posture orientation can be standing, lying, sitting, etc. it should be noted that the motion and posture data is used as input to the analysis algorithm for the determination of the appropriate thresholds to determine an abnormal state.
Step 350: analyzing the sensed data.
  The sensed data is analyzed by remote-processor 510. To continue the example, the measured level of acoustic noise coming from the lung is transmitted to remote-processor 510. For example, in a function that matches, using pattern recognition algorithms, acoustic noises detected from the lungs to known patterns that indicate CHF problems, the processing unit calculates:
IF {acoustic measurement}=MATCHING {[Crackles, crepitations, rales] patterns}
AND IF {acoustic noise level}<ANL db;
(where ANL=adjusted acoustic noise level)
[NOTE: typically, there is a function that adjusts the background acoustic noise so that the environment does not interfere with the real signal]
AND IF |{acoustic measurement}-{reference acoustic measurement}|>X1 parameter
[NOTE: there is at least one reference acoustic sensor that is far from the lung for comparison. Hence, if the signals are substantially the same, it likely that the measured acoustic noise is an environment acoustic noise]
AND sufficient time elapsed since last identical state identified,
THEN send an alert type j to the alerting unit (150 or 250.
Step 360: determining if the sensed data is abnormal.
  If the sensed data is within the normal range, go to step 310.
Step 370: selecting a proper alert type.
  It has been determined that the sensed data is abnormal. To continue the example, an alert type j or k is set.
Step 380: issuing an alert.
  Remote-processor 510 issues a personal-alert 550 according to the selected alert type. To continue the example, the alert type is a vocal 'beep' and sending an SMS message to a predetermined phone number.
  Go to step 310.
(end of steps details of process 300)

Figure 6:
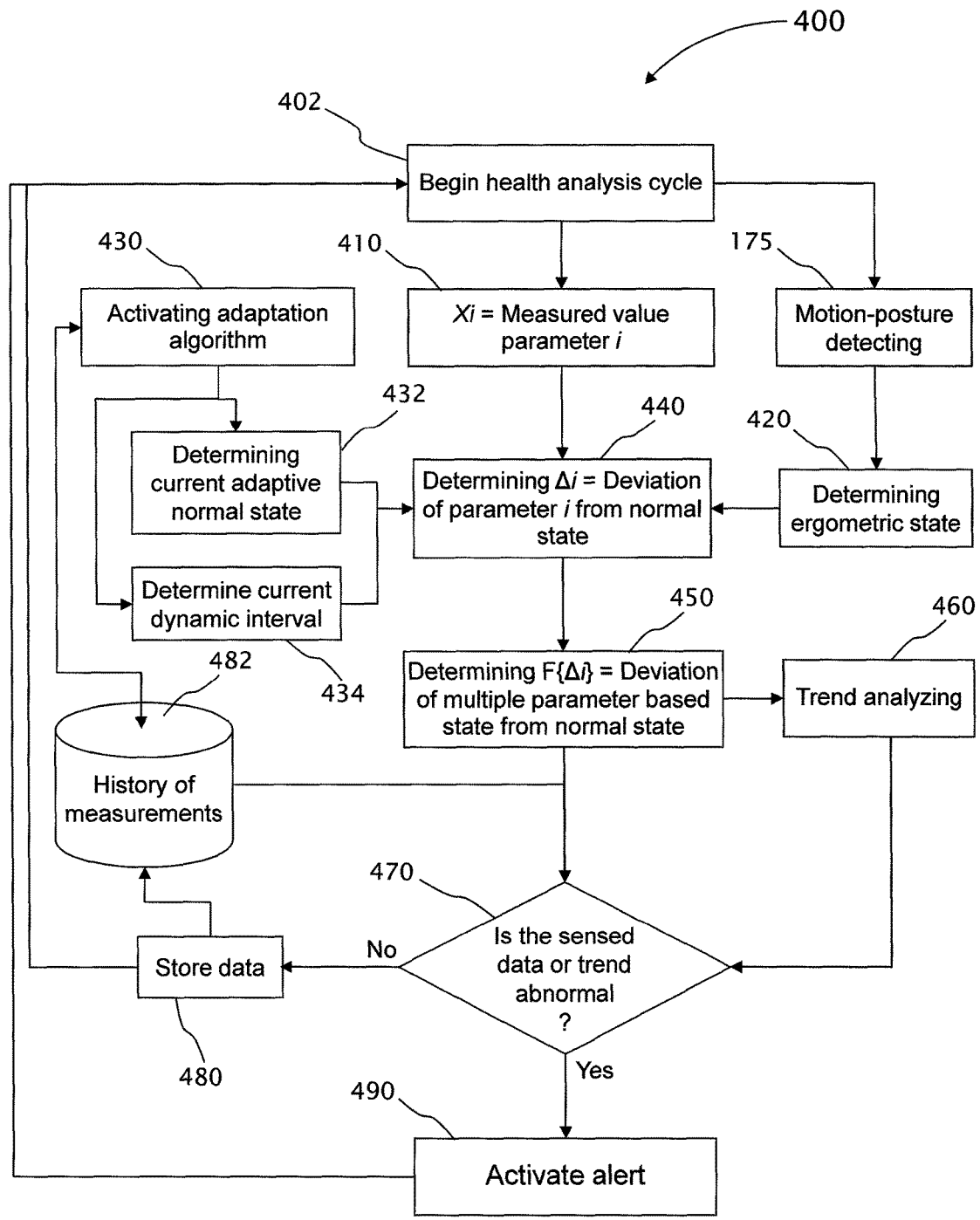
FIG. 6 is a schematic flow diagram that outlines a cycle of monitoring the health status of a living being.

Reference is now made to FIG. 6, which is a schematic flow diagram that outlines a cycle 400 of monitoring the health status of a living being, according to variations of the present invention. Cycle 400 begins in virtual step 402 and proceeds in the following steps:
Step 410: sensing designated health related parameter, thereby generating sensed data.
  Each sensor$_i$ senses the parameter that a sensor$_i$ is designed to measure, and thereby generating sensed data Xi.
Step 420: determine ergometric state.
  The ergometric state of the monitored living being is determined, that is the motion state and the bodily orientation of the monitored living being.
Step 430: perform data analysis using adaptation algorithm.
  Remote-processor 510 activates an adaptation algorithm to compute the following:
Step 432: determine the current adaptive normal state.
  Determine the current normal state of the monitored living being, adjusted to a variety of personal parameters of the monitored living being. The History of measurements of the monitored living being is obtained from database 482.
Step 434: determine the current dynamic interval.
  Determine the current dynamic interval of the monitored living being, forming the envelope in which the health state of the monitored living being is considered normal and out of which the health state of the monitored living being is considered abnormal. The History of measurements of the monitored living being is obtained from database 482.
Step 440: determine the deviation of the measured value Xi from normal state.

The deviation Δi of the measured value Xi from normal state is determined.

Step 450: determine the deviation of a group of measured values, from normal state.

The deviation F{Δi} a group of measured values from normal state is determined.

Step 460: perform trend analysis.

A trend analysis performed to compute the deviation a trend from normal state.

Step 470: determining if the sensed data or trend is abnormal.

If the sensed data or trend is determined to be abnormal, go to step 490.

Step 480: store data.

Store all sensed data and computed data in database 482. Go to step 402.

Step 490: activating an alert.

The sensed data or trend is determined to be abnormal and therefore, a personal-alert 550 is issued.

Go to step 402.

(end of steps details of cycle 400)

Another aspect of the present invention includes outlining a method for determining the personal-alert level for a monitored living being and issuing a respective personal-alert upon detecting a potentially health hazardous situation.

Figure 7:
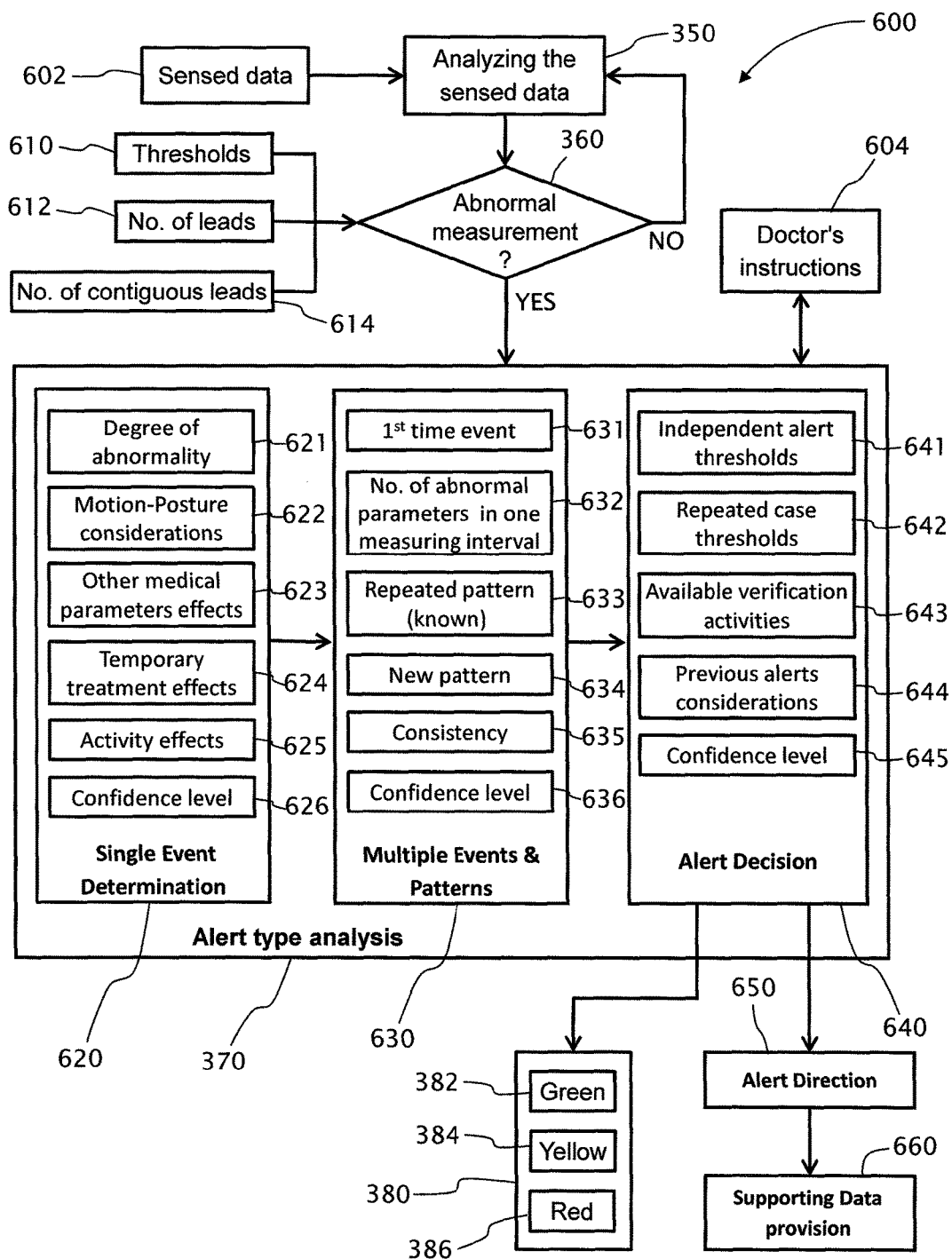
FIG. 7 is a schematic flow diagram that detailing the analysis of alert type decision making, shown generally in FIG. 5.

Reference is made to FIG. 7, a schematic flow diagram 600 that outlines the steps of determining the alert level for a monitored living being 10, performed for example on a system combining monitoring garment 100 and mobile device 500, and the steps leading to issuing a personal-alert upon detecting a potentially health hazardous situation. The assignment of tasks to garment-processor 112 and remote-processor 510 is given by way of example only, with no limitation, and tasks may be subdivided between these two processors in any other way.

Method 600 begins by providing (step 602) step 350 of analyzing the sensed data with the sensed data, performed by garment-processor 112. In step 360, garment-processor 112 determines if the sensed data is abnormal, based, among other things, on thresholds (either manually set or as an output from the adaptive steps 432 and 434) data 610, the number of leads 612 in the ECG measuring sub-unit, and the number of contiguous leads 614, where the abnormality was sensed. If the sensed data is not within the normal range, method 600 proceeds with step 370 of selecting a proper personal-alert type/level, typically performed by remote-processor 510. Step 370 includes the following steps:

Step 620: determining abnormality level, based on a single event.

Remote-processor 510 analyzes the particular abnormal sensed data, without taking into account biasing data such as history of events, personal doctor's instructions, etc. Typically, in this step, the analysis may take into account one or more of the following feature, or a combination thereof:

Degree (quantity) of abnormality (621).
Motion-Posture considerations (622).
Other medical parameters effects (623) such as other measured parameters.
Temporary treatment effects (624) such as medication that user 10 is taking.
Activity effects (625) such as sleeping or eating.
Confidence level (626).
Others.

Step 630: determining abnormality level, based multiple events & patterns.

Remote-processor 510 further analyzes the particular abnormal sensed data, taking into account biasing data such as history of events and multiple abnormal patterns. Typically, in this step, the analysis may take into account one or more of the following feature, or a combination thereof:

$1^{st}$ time event (631).
The number of abnormal parameters in one measuring interval (632).
Repeated pattern (known) (633).
A new pattern (634).
Consistency (635).
Confidence level (636).
Others.

Step 640: making a final decision.

Remote-processor 510 further analyzes the particular abnormal sensed data, taking into account biasing data such as history of events and multiple abnormal patterns. Typically, in this step, the analysis may take into account one or more of the following feature, or a combination thereof:

Independent alert thresholds (641).
Repeated case thresholds (642).
Available verification activities (643).
Previous alerts considerations (644), for example, may instruct "alert only if a new type of abnormality", "wait X minutes before issuing same alert").
Confidence level (645).
Others.

Optionally, a personal physician, who is familiar with the health status of living person 10, may enter (preliminary step 604) thresholds and conditions/circumstance, in which a yellow or red personal-alerts are to be issued, optionally including notifying the physician, upon such issue of a personal-alert. Optionally, remote-processor 510 updates the personal physician of living person 10 with sensed data, raw or analyzed.

Step 380: issuing a personal-alert.

Remote-processor 510 issues a personal-alert 550 according to the selected alert type, for example:

A green-alert level—meaning no alert is issued, as the analysis has determined that the suspected abnormal parameter is within "normal range" for living person 10. [

It should be noted that this is a normal state. Typically, no sensed data will be sent by garment-processor 110 that is clearly a 'green-alert level' data.

A yellow-alert level (optional)—meaning that a personal-alert is issued, advising living being 10 to seek medical advice, for example, 'call your doctor'.

A red-alert level (optional)—meaning that a personal-alert is issued, urging living being 10 to seek immediate medical help, for example, 'go to hospital'.

Step 650: distributing the personal-alert.

Optionally, typically for red-alert and yellow-alert level personal-alerts, remote-processor 510 distributing the personal-alert to preconfigured target entities, such as a pre-selected relative of living being 10, to an emergency service provider and/or any other pre-selected target entity.

Step 660: Supporting Data provision.

Optionally, typically for red-alert and yellow-alert level personal-alerts, remote-processor 510 distributing the sensed data, raw and or analyzed data, to preconfigured target entities, such as an emergency service provider, while living being 10 is being evacuated for treatment, and/or the personal physician of living being 10, or any other pre-selected target entity.

Go to step 310.

(end of steps details of process 600)

Figure 9:
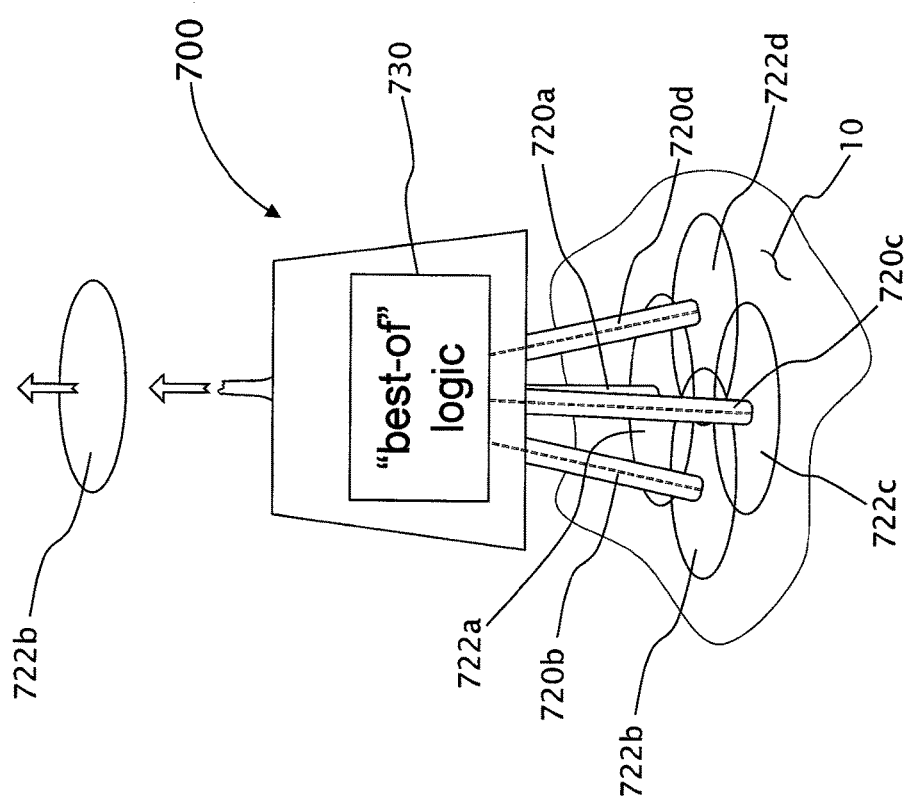
FIG. 9 illustrates a schematic illustration of the logic of the probe device shown in FIG. 8.
Figure 8:
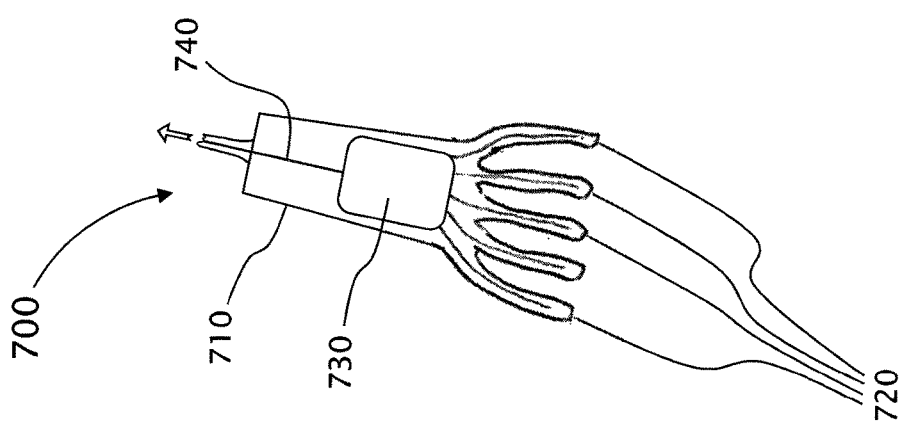
FIG. 8 illustrates an example probe device, having a multiplicity of electrodes and a processor, according to embodiments of the present invention.

Reference is also made to FIG. 8, an example probe device 700, having a multiplicity of electrodes 720, according to embodiments of the present invention; and to FIG. 9, schematically illustrating the logic of probe device 700. Probe device 700 further includes a probe-processor 730 facilitating selection of the best sensed signal 722. Upon activation of probe device 700 (typically by local processing unit 110), all electrodes 720 transmit the currently sensed data 722 to probe-processor 730. Probe-processor 730 analyzes the individual sensed data, selects the best sensed data and transmits the "best" sensed-signal as the output of the probe device, typically, to local processing unit 110. The "best" sensed-signal is transmitted via line 740 or wirelessly. In the example shown in FIG. 9, sensed data 722b, as sensed by electrode 720b, is selected as the "best" sensed data 722 and transmitted, typically, with no limitation, to local processing unit 110.

The "best" sensed-signal 722 is selected according to a pre-configured method. In one embodiment, the pre-configured method may by comparing each sensed data 722 to a "normal" signal and selecting the signal best matching the "normal" signal. The "normal" signal may be, for example, the average normal signal of the monitored user 10, or of people of the same gender of person 10, or of people of the same age group of person 10, or a combination thereof, other criteria. The "normal" signal may also be the healthy normal signal as set by the physician of person 10.

An aspect of the present invention includes providing a method for controlling a multiplicity of probe devices 700 embedded in a monitoring-garment 100. Probe devices 700 are activated in a preconfigured sequence, which sequence may be dynamically adapted to the health status of the monitored person 10. For example, when a sensor detects sensed data 722 that is nearly out of normal range or is slightly out of normal range, the sensing frequency of that sensor, and possibly other related sensors, is increased.

Figure 10:
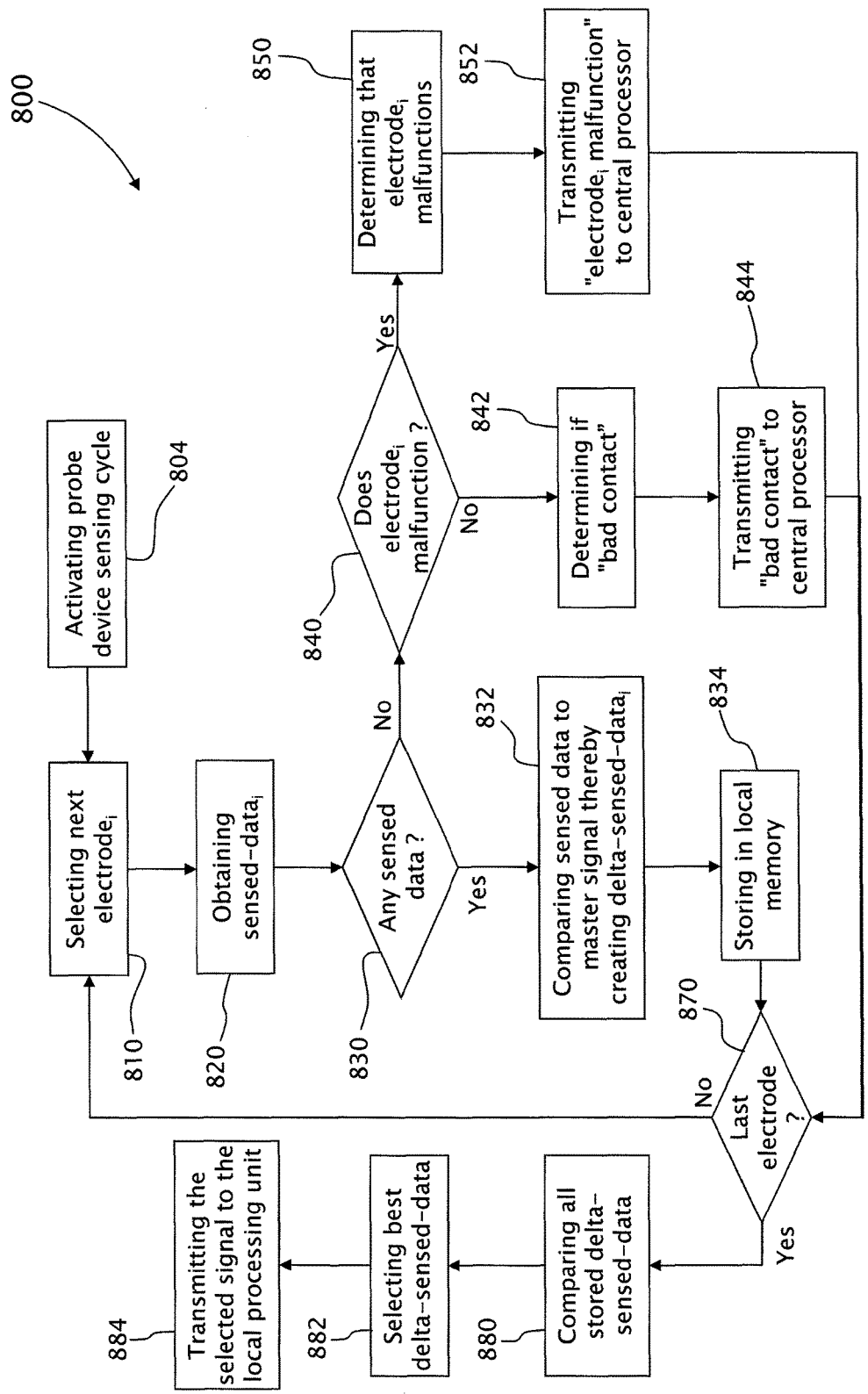
FIG. 10 is a schematic flow diagram that outlines the steps of an exemplary cyclic sensing method, similar to the as in FIG. 4, wherein the sensors are probe devices, having a multiplicity of electrodes.

Reference is made to FIG. 10, which is a schematic flow diagram 800 that outlines the steps of an exemplary cyclic sensing method, similar to method 200, preferably performed by garment-control device 110 and assisted by probe-processor 730 of each probe device 700, and the steps of preliminarily analyzing and sorting-out the sensed data 722. Method 800 begins by activating the next probe device 700 by local processing unit 110 (step 804). Method 800 proceeds with the following steps:

Step 810: selecting the next electrode.
  Probe device 700 is activated according to the currently configured sequential order and thereby, each electrode 720 is activated in a preconfigured order.

Step 820: obtaining sensed data from each electrode.
  Sensed data 722 is obtained from each electrode 720 by probe-processor 730.

Step 830: probe-processor 730 analyzes the sensed data 722.
  Probe-processor 730 determines if the sensed data 722 is null.
  If sensed data 722 is null, go to step 840.

Step 832: comparing each sensed data to a master signal thereby creating delta-sensed-data for each respective electrode.
  Probe-processor 730 compares the sensed data 722, sensed by each electrode 720, to a master signal, thereby creating a delta-sensed-data for each respective electrode 720.

Step 834: storing computed delta-sensed-data of each electrode 720 in the memory of probe-processor 730.
  The computed delta-sensed-data of each electrode 720 is stored in the memory of probe-processor 730.
  Go to step 870.

Step 840: determining if an electrode 720 malfunctions.
  Probe-processor 730 determines if an electrode 720 malfunctions.
  If the electrode 720 malfunctions, go to step 250.

Step 842: determining if "bad contact".
  Probe-processor 730 determines that sensed data 722 is null because of "bad contact".

Step 844: transmitting "bad contact" to local processing unit 110.
  Probe-processor 730 transmits "bad contact" for the electrode 720 to local processing unit 110.
  Go to step 870.

Step 850: Determining that an electrode 720 malfunctions.
  Probe-processor 730 determines that an electrode 720 malfunctions.

Step 852: transmitting "bad contact" to local processing unit 110.
  Probe-processor 730 transmits "bad contact" for the electrode 720 to local processing unit 110.

Step 870: determining if the last electrode 720 is the last electrode of probe device 700.
  If the last electrode 720 is not the last electrode of probe device 700, go to step 810.

Step 280: comparing all stored delta-sensed-data.
  Probe-processor 730 compares all stored delta-sensed-data.

Step 882: selecting best delta-sensed-data.
  Probe-processor 730 determines the best delta-sensed-data and selects the signal of the electrode 720 associated with the determined best delta-sensed-data.

Step 884: transmitting the selected signal to local processing unit 110.
  Probe-processor 730 transmits the selected signal to local processing unit 110.

(end of steps details of cyclic process 800)

Preferably the health monitoring and self-alert system, including monitoring garment 100, complies with to the IEEE 802.15 standard or an updated standard and FCC Medical Body Area Network (MBAN) systems or an updated standard.

It should be further noted that the monitoring of the health condition is performed continuously. Personal-alerts are generated immediately as a dangerous situation is detected. The user does not have to perform any activity action in order to get the alert. For the sake of clarity, activity may be required at installation time, but not during monitoring.

It should be further noted that personal-alerts can be issued to the monitored being and/or to an external entity, such as an emergency center, a close relative, etc. The personal-alert can be transmitted to a computer, a telephone and/or any other communication device.

It should be further noted that the health monitoring and self-alert system can optionally send the data to any remote processor, which can further process the information, compare it to many other monitored people, make statistics-based decisions and other decision-making methods to improve alerts sensitivity and specificity and providing information for the treatment of the living being once getting to a treating facility.

Preferably, a calibration application is performed by remote-processor 510, garment processor 112 or a combination thereof, when monitoring garment 100 is first fitted to living being 10. Optionally, the calibration application (or a derivation thereof) is also performed after wearing monitoring garment 100 by living being 10.

Figure 11:
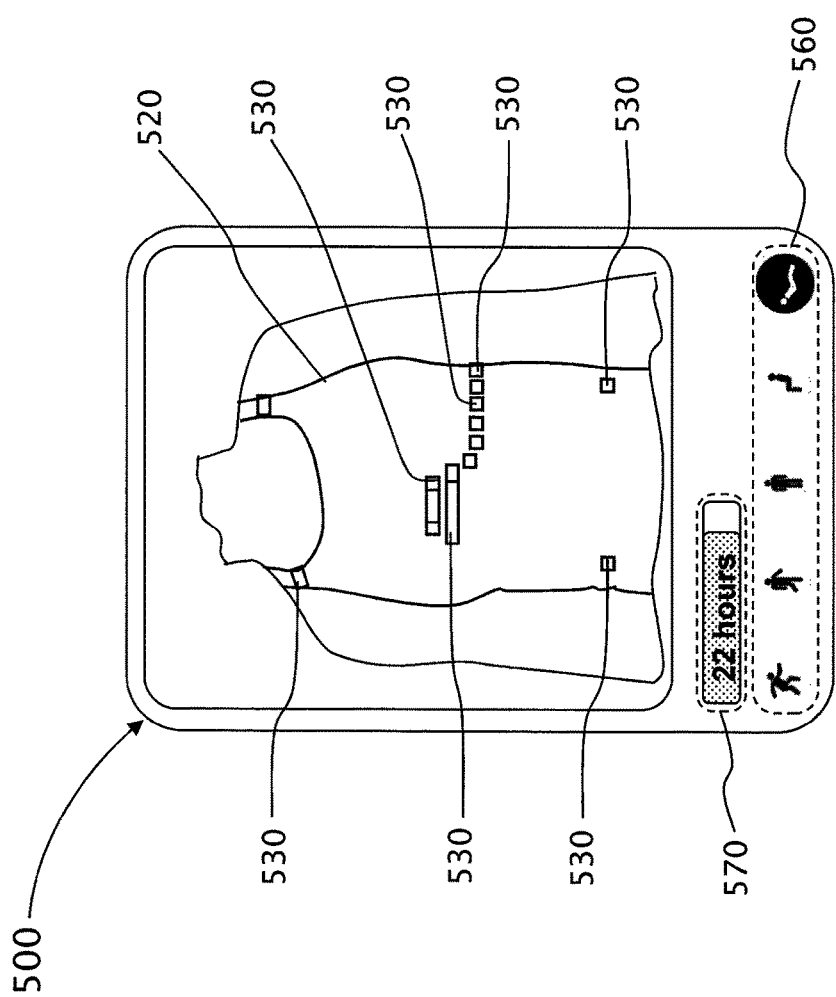
FIG. 11 illustrates an example calibration application for verifying the positioning of the sensors, performed by the mobile device shown in FIG. 1.

Reference is also made to FIG. 11, illustrating an example calibration application for verifying the positioning of the sensors (120, 130, 140, 150 and 160), performed on mobile device 500. The application displays a garment-body illustration 520 of garment-body 102 of monitoring-garment 100, wherein respective sensors icons 530 are superimposed over garment-body illustration 520. Remote-processor 510 receives sensed data, obtained by garment processor 112 from each of the sensors (120, 130, 140, 150 and 160), and analyzes the sensed data to thereby determine if the received signal is good or bad, based on preconfigured parameters. An indication, for each of the sensors (120, 130, 140, 150 and 160) is then displayed on the display of mobile device 500. For example, if the signal is determined to be good, the icon (530) of the respective sensor is colored in green, and if the signal is determined to be bad, the icon (530) of the respective sensor is colored in red.

In FIG. 11, also illustrated is an optional indication 570 of the battery status. Also illustrated are optional indications 560 regarding the motion and posture states of monitored living being 10, as detected by garment-control device 110. User 10 may compare his/her current position to the one detected by garment-control device 110, as displayed (560) on the display of mobile device 500.

The invention being thus described in terms of embodiments and examples, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for monitoring the health status of a living being and issuing a personal-alert upon detecting a potentially health hazardous situation, comprising the steps of:
    a) providing a seamless independent wearable health monitoring and self-alert system, configured for use by living being on a daily basis, including a healthy living being, the system comprising:
        i. a garment worn by the living being adjacently to preconfigured portions of the body of the living being;
        ii. a garment-processor;
        iii. multiple sensing devices selected from the group consisting of sensors, accelerometers and electrodes;
        iv. a remote-processor;
        v. a transmitter; and
        vi. an alerting unit,
    wherein at least one of said sensing devices is embedded into said garment;
    wherein each of said sensing devices is configured to detect a predetermined physiological or chemical parameter of the living being;
    wherein said garment-processor is in operational communication flow with said sensing devices and said remote-processor;
    wherein said remote-processor is built into a personal mobile device, such as a smart-phone, coupled with the living being;
    wherein said garment-processor is adapted to receive said ECG-parameters and/or said detected parameters and transmit said received parameters by said transmitter to said remote-processor;
    b) sensing designated health related parameter by said sensors, thereby obtaining sensed data;
    c) analyzing said sensed by said garment-processor, to thereby create analyzed sensed data;
    d) determining if said analyzed sensed data is abnormal;
    e) if said analyzed sensed data is determined to be abnormal, transmitting said analyzed sensed data to said remote-processor; and
    f) activating said alert unit by said remote-processor to thereby issue a personal-alert to the living being, in real time,
    wherein said remote-processor further analyzes said analyzed sensed data, to thereby determine if to issue a personal-alert and optionally, determining the level of said personal-alert.

2. The health monitoring and self-alert system as in claim 1, wherein said determining if said analyzed sensed data is abnormal, includes considering the current motion-posture state of the living being.

3. The health monitoring and self-alert method as in claim 1, wherein said determining if said analyzed sensed data is abnormal, includes considering respective threshold values, number of leads, number of contiguous leads or a combination thereof.

4. The health monitoring and self-alert method as in claim 1, wherein said determining said level of said personal-alert is determined based on a single health related event, multiple health related events, health related patterns or a combination thereof;
    wherein said single health related event includes biasing data selected from the group including: degree of abnormality, motion and posture considerations, temporary treatment effects, activity effects and confidence level; and
    wherein said multiple health related events, health related patterns include biasing data selected from the group including: first or repeated event, number of abnormal parameters in one measuring interval, repeated known pattern, new pattern, consistency and confidence level.

5. The health monitoring and self-alert method as in claim 1, wherein said determining said level of said personal-alert is determined based on personal data pre-entered by a professional person, acquainted with the living being.

6. A method for preliminarily analyzing and sorting-out sensed data obtained by multiple sensors, comprising the steps of:
    a) providing a seamless independent wearable health monitoring and self-alert system, configured for use by living being on a daily basis, including a healthy living being, the system comprising:
        i. a garment worn by the living being adjacently to preconfigured portions of the body of the living being;
        ii. a garment-processor; and
        iii. multiple sensing devices selected from the group consisting of sensors and electrodes,
    wherein at least one of said sensing devices is embedded into said garment;
    wherein each of said sensing devices is configured to detect a predetermined physiological or chemical parameter of the living being;
    wherein said garment-processor is in operational communication flow with said sensing devices; and
    wherein said garment-processor activates said sensors in cycles having a preconfigured time interval; and b) activating said sensors, by said garment-processor, in cycles having a preconfigured sequence and time interval, wherein each cycle comprises the steps of:
   i. selecting next $sensor_i$;
   ii. obtaining sensed data from said $sensor_i$;
   iii. determining if said sensed data is abnormal; and
   iv. if said sensed data is determined to be abnormal, transmitting said sensed data to a preconfigured target receiver.

\* \* \* \* \*